(12) United States Patent
Takahashi et al.

(10) Patent No.: US 6,552,219 B1
(45) Date of Patent: Apr. 22, 2003

(54) PROCESS FOR THE PREPARATION OF VITAMIN A, INTERMEDIATES, AND PROCESS FOR THE PREPARATION OF THE INTERMEDIATES

(75) Inventors: Toshiya Takahashi, Ibaraki (JP); Atsushi Furutani, Oita (JP); Shinzo Seko, Toyonaka (JP)

(73) Assignee: Sumitomo Chemical Company, Ltd., Osaka (JP)

( * ) Notice: Subject to any disclaimer, the term of this patent is extended or adjusted under 35 U.S.C. 154(b) by 0 days.

(21) Appl. No.: 09/701,873

(22) PCT Filed: Apr. 3, 2000

(86) PCT No.: PCT/JP00/02146

§ 371 (c)(1),
(2), (4) Date: Dec. 5, 2000

(87) PCT Pub. No.: WO00/59860

PCT Pub. Date: Oct. 12, 2000

(30) Foreign Application Priority Data

Apr. 5, 1999 (JP) .............................. 11-097569
May 20, 1999 (JP) ........................... 11-140294

(51) Int. Cl.[7] .................. C07C 67/00; C07C 35/04; C07C 35/02
(52) U.S. Cl. ............... 560/260; 560/262; 560/259; 568/28; 568/824
(58) Field of Search ................... 568/28, 31, 824; 560/129, 259, 260, 262

(56) References Cited

U.S. PATENT DOCUMENTS 4,825,006 A    4/1989  Otera et al.
4,876,400 A   10/1989  Otera et al.
4,977,001 A    8/1990  Onishi et al.
5,527,952 A *  6/1996  Kuroda et al. .............. 560/262

FOREIGN PATENT DOCUMENTS

EP    0 900 785   *  3/1999
JP    B2 561265      9/1993
JP    B2 43389       1/1999

OTHER PUBLICATIONS

C. Mercier et al. "Organometallic chemistry in industrial vitamin A and vitamin E Synthesis" Pure & Appl. Chem., vol. 66, No. 7, pp. 1509–1518, 1994.

* cited by examiner

*Primary Examiner*—Jean F. Vollano
(74) *Attorney, Agent, or Firm*—Birch, Stewart, Kolasch & Birch, LLP

(57) ABSTRACT

There are provided a dihalogen derivative represented by formula (2):

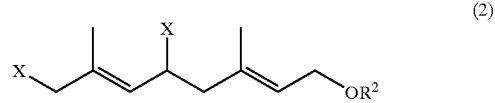

wherein X represents a halogen atom and $R^2$ represents a protective group for a hydroxyl group; a process for producing the same; and a process for producing vitamin A by use of said dihalogen derivative.

12 Claims, 5 Drawing Sheets

PROCESS FOR THE PREPARATION OF VITAMIN A, INTERMEDIATES, AND PROCESS FOR THE PREPARATION OF THE INTERMEDIATES

This application is the national phase under 35 U.S.C. § 371 of PCT International Application No. PCT/JP00/02146 which has an International filing date of Apr. 3, 2000, which designated the United States of America.

TECHNICAL FIELD

The present invention relates to a process for producing vitamin A which is important in the fields of pharmaceutical preparations, feed or food additives, intermediates thereof, and a process for producing the same.

1. Background Art

As conventional processes for producing vitamin A, there have been known a method of a carbon-increment reaction in a side chain of β-ionone (C13) as a starting material (Pure & Appl. Chem. 66, 1509 (1994)) and a method of coupling C10 sulfones with C10 aldehydes and then eliminating the sulfone group (JP-B 4-3388, JP-B 5-61265 etc.). In the former method, however, β-ionone (C13) as the starting material is very expensive on the market, and in the latter method, a very expensive acetaldehyde derivative is used as an oxidizing agent particularly in an oxidation step in a process for producing the C10 aldehyde, and thus these methods are not always industrially excellent methods.

2. Disclosure of the Invention

Under these circumstances, the present inventors have extensively studied to develop a process for producing vitamin A from inexpensive starting materials, and as a result, they have found that a novel dihalogen derivative can be readily obtained from a triene derivative which can be readily and economically produced from C10 alcohols such as geraniol or linalool. They have also found that vitamin A can be produced via sulfone derivatives from said dihalogen derivatives, thus arriving at the present invention.

That is, the present invention provides:

1. a dihalogen derivative represented by formula (2):

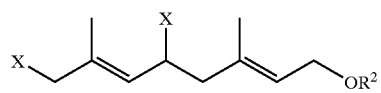

(2)

wherein X represents a halogen atom and $R^2$ represents a protective group for a hydroxyl group, 2. a process for producing a dihalogen derivative represented by formula (2) above, which comprises allowing a halogenating agent to react with a triene derivative represented by formula (4):

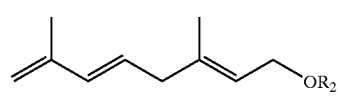

(4)

wherein $R^2$ represents a protective group for a hydroxyl group, 3. a process for producing a sulfone derivative represented by formula (1):

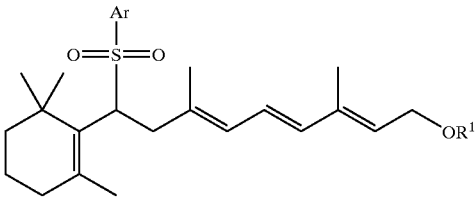

(1)

wherein Ar represents an aryl group which may have a substituent group, and $R^1$ represents a hydrogen atom or a protective group for a hydroxyl group, which comprises allowing a sulfone represented by formula (3):

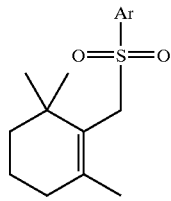

(3)

wherein Ar represents an aryl group which may have a substituent group, to react in the presence of a base with a dihalogen derivative represented by formula (2) above, 4. a sulfone derivative represented by formula (1) above, and 5. a process for producing vitamin A, which comprises allowing a sulfone derivative represented by formula (1) above to react with a base.

MODE FOR CARRYING OUT THE INVENTION

Figure 1:
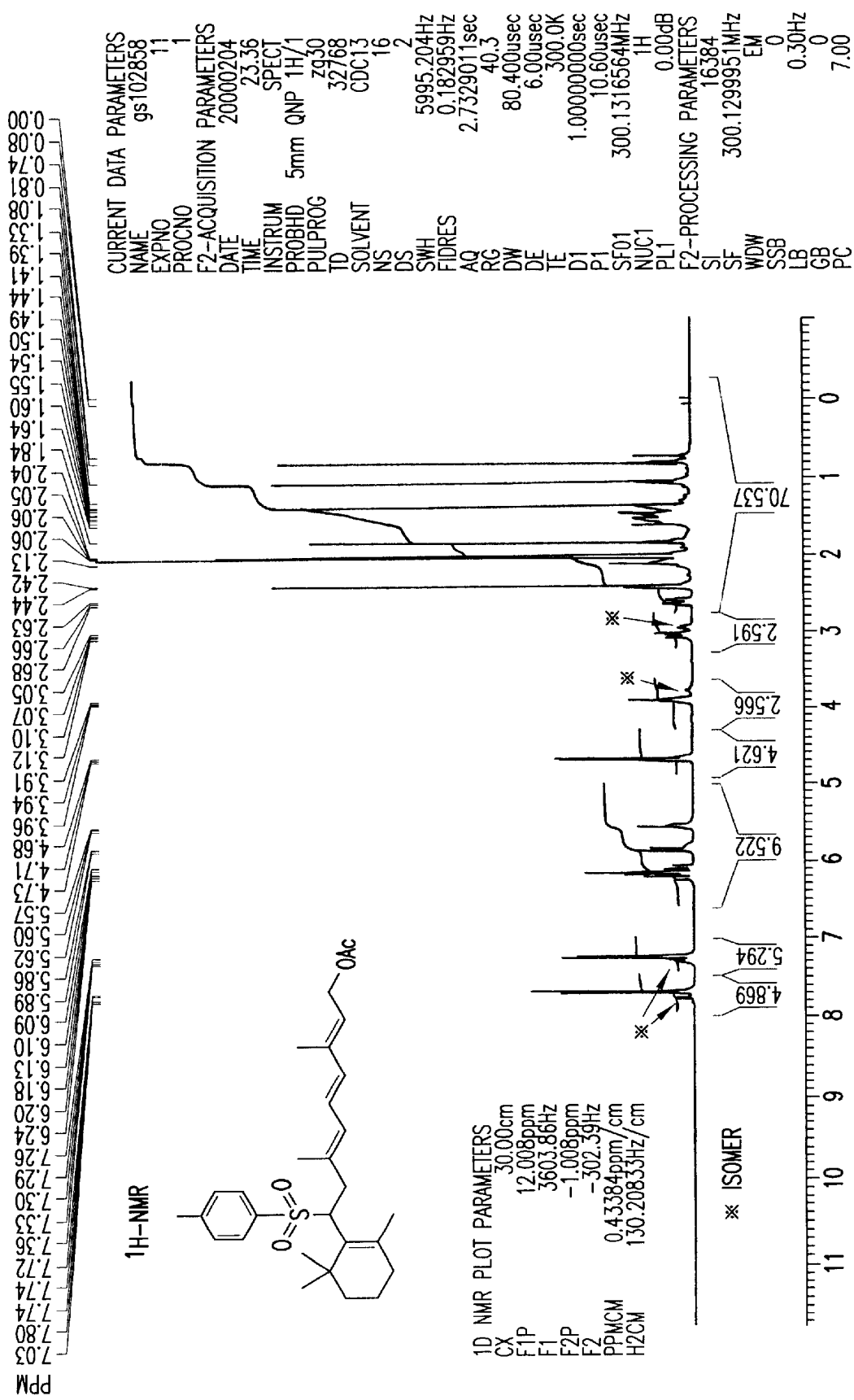
FIG. 1 is a $^1$H—NMR spectrum of the sulfone derivative (III) described in the Examples.
Figure 2:
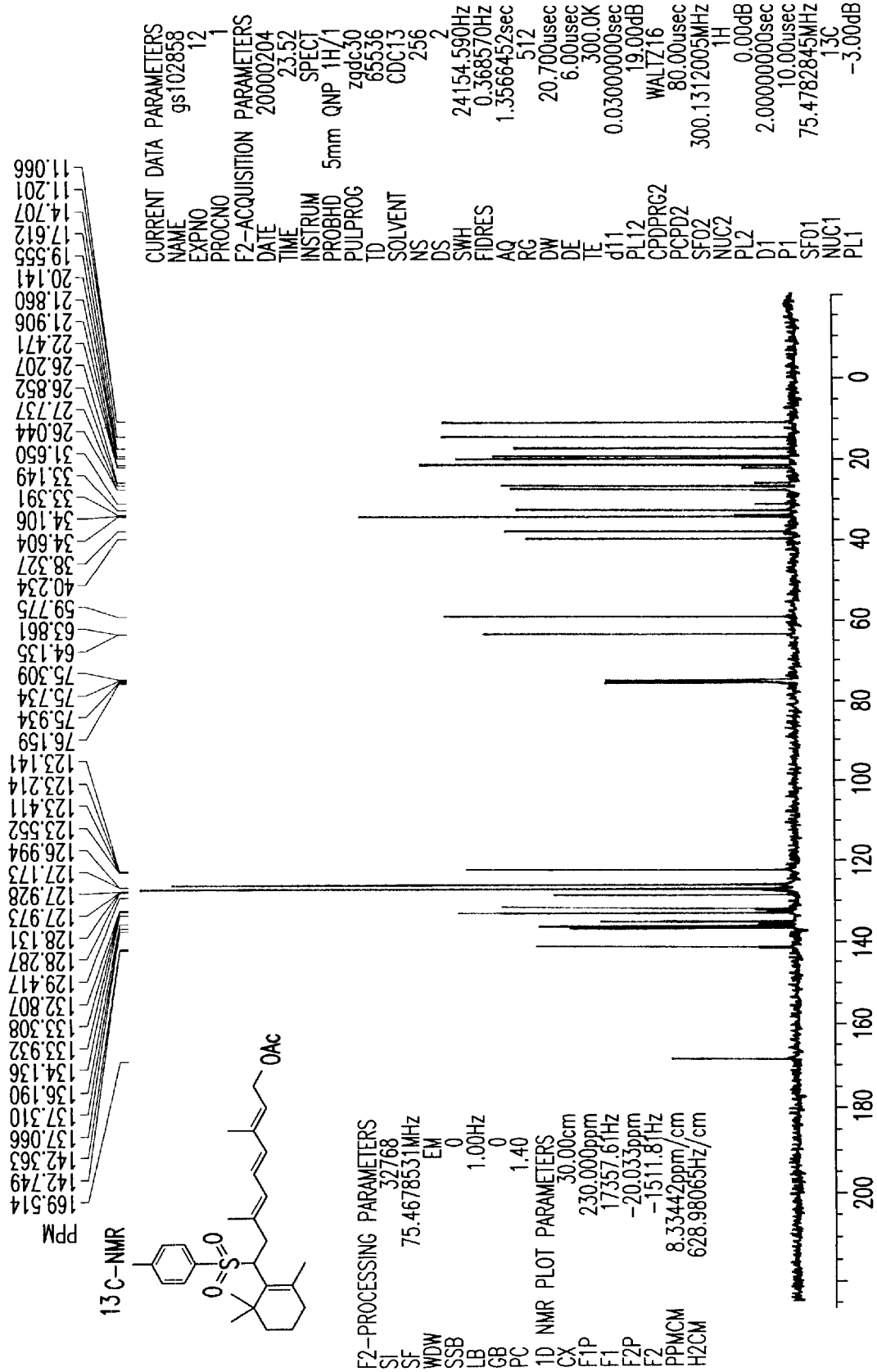
FIG. 2 is a $^{13}$C—NMR spectrum of the sulfone derivative (III) described in the Examples.
Figure 3:
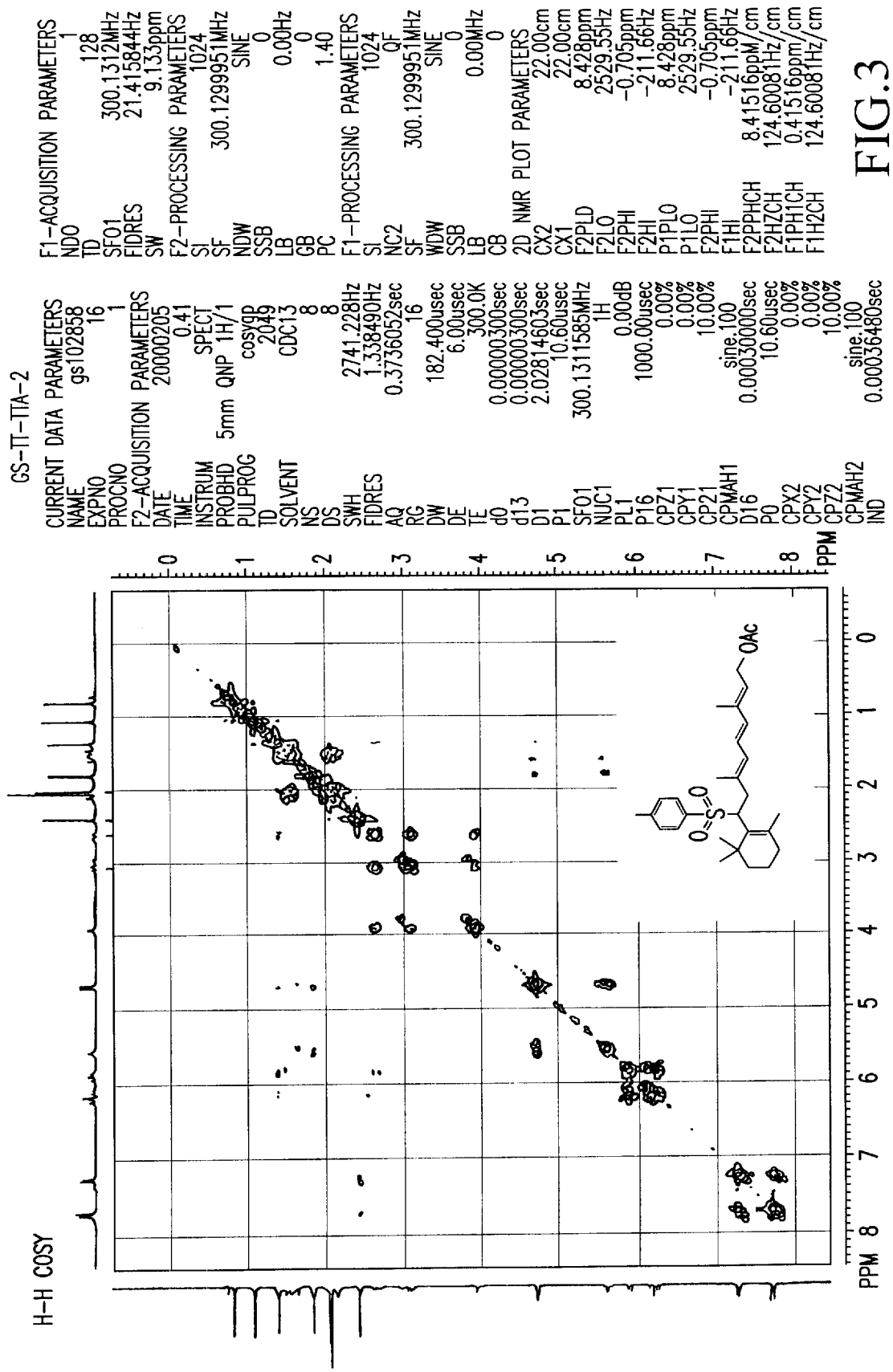
FIG. 3 is an H—H COSY spectrum of the sulfone derivative (III) described in the Examples.
Figure 4:
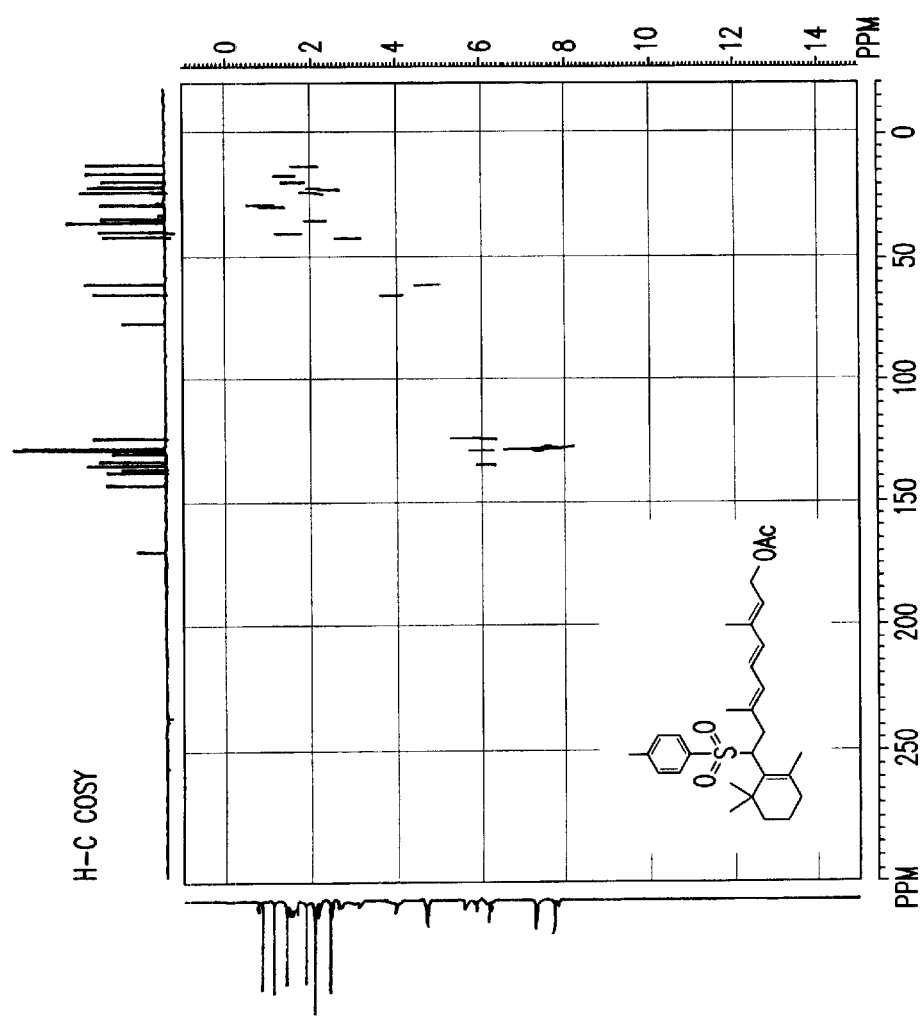
FIG. 4 is an H—C COSY spectrum of the sulfone derivative (III) described in the Examples.
Figure 5:
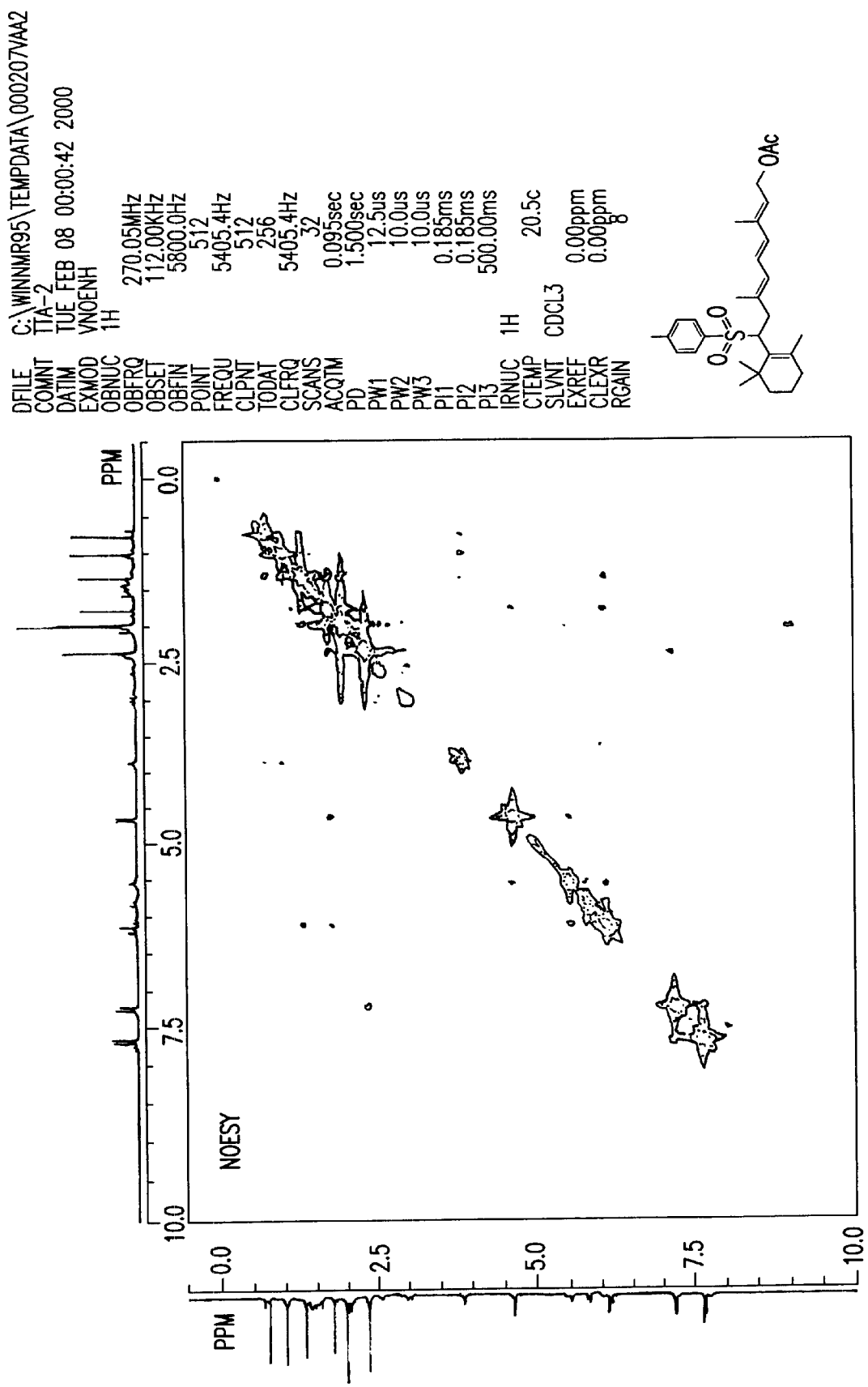
FIG. 5 is an NOESY spectrum of the sulfone derivative (III) described in the Examples.

Hereinafter, the present invention is described in detail.

The substituent group $R^1$ in formula (1) represents a hydrogen atom or a protective group for a hydroxyl group, and the substituent group $R^2$ in formulae (2) and (4) represents a protective group for a hydroxyl group. Examples of the protective group for a hydroxyl group in both groups include an acyl group which may be substituted, a tri-substituted silyl group, a saturated or unsaturated hydrocarbyloxycarbonyl group which may be substituted, an alkoxymethyl group, a benzyl group which may be substituted, and a group having tertiary carbon substituted with an aryl or alkyl group.

Examples of the acyl group which may be substituted include a C1–C7 acyl group (e.g. an alkanoyl group, or a benzoyl group) which may be substituted with a substituent group selected from a halogen atom, a (C1–C3) alkoxy group, a (C1–C3) alkanoyloxy group, a nitro group and a hydroxyl group Specific examples thereof include a formyl, acetyl, ethoxyacetyl, fluoroacetyl, difluoroacetyl, trifluoroacetyl, chloroacetyl, dichloroacetyl, trichloroacetyl, bromoacetyl, dibromoacetyl, tribromoacetyl, propionyl, 2-chloropropionyl, 3-chloropropionyl, butyryl, 2-chlorobutyryl, 3-chlorobutyryl, 4-chlorobutyryl, 2-methylbutyryl, 2-ethylbutyryl, valeryl, 2-methylvaleryl, 4-methylvaleryl, hexanoyl, isobutyryl, isovaleryl, pivaloyl, benzoyl, o-chlorobenzoyl, m-chlorobenzoyl, p-chlorobenzoyl, o-hydroxybenzoyl, m-hydroxybenzoyl, p-hydroxybenzoyl, o-acetoxybenzoyl, o-methoxybenzoyl, m-methoxybenzoyl, p-methoxybenzoyl, p-nitrobenzoyl group and the like.

The tri-substituted silyl group includes silyl groups substituted with 3 substituent groups selected from a phenyl group and a (C1–C4) alkyl groups.

Specific examples of such a silyl group include a trimethylsilyl, triethylsilyl, t-butyldimethylsilyl, t-butyldiphenylsilyl group and the like.

Examples of the alkoxymethyl group include tetrahydropyranyl, methoxymethyl, methoxyethoxymethyl and 1-ethoxyethyl.

Examples of the saturated or unsaturated hydrocarbyloxycarbonyl group which may be substituted include a (C1–C4) alkoxycarbonyl group which may be substituted with a halogen atom or atoms (e.g., a methoxycarbonyl group, an ethoxycarbonyl group, a 2,2,2-trichloroethoxycarbonyl group), and an allyloxycarbonyl group.

Examples of the benzyl group which may be substituted include a p-methoxybenzyl group and a benzyl group.

Examples of the group having a tertiary carbon substituted with an aryl or alkyl include a group having a tertiary carbon substituted with 3 substituent groups selected from an aryl group (e.g. phenyl group) and a (C1–C3) alkyl group, and specific examples thereof include a trityl group and a t-butyl group.

Examples of the substituent group Ar in formulae (1) and (3) include an aryl group which may have substituent group. Examples of said aryl group include a phenyl group and a naphthyl group, and the examples of the substituent group include a C1 to C5 straight-chain or branched alkyl group, C1 to C5 straight-chain or branched alkoxy group, a halogen atom and a nitro group.

Examples of the substituent group Ar include a phenyl, naphthyl, o-tolyl, m-tolyl, p-tolyl, o-methoxyphenyl, m-methoxyphenyl, p-methoxyphenyl, o-chlorophenyl, m-chlorophenyl, p-chlorophenyl, o-bromophenyl, m-bromophenyl, p-bromophenyl, o-iodophenyl, m-iodophenyl, p-iodophenyl, o-fluorophenyl, m-fluorophenyl, p-fluorophenyl, o-nitrophenyl, m-nitrophenyl, p-nitrophenyl group and the like.

The halogen atom represented by X includes a chlorine atom, a bromine atom and an iodine atom. Preferred is a bromine atom.

The triene derivatives of formula (4) used as a starting compound in the present invention can be produced from geraniol or linalool according to a reaction route shown in e.g. the following scheme 1 (JP-A 11-130730).

Scheme 1

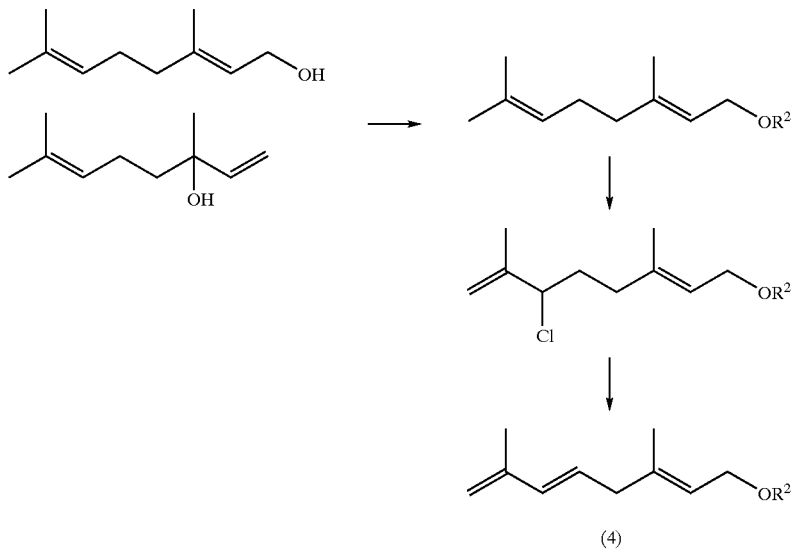

(4)

The sulfone of formula (3) used as another starting compound in the present invention can be produced by a method shown in Chemistry Letters 479 (1975).

The dihalogen derivative of formula (2) in the present invention can be produced by allowing a halogenating agent to react with the triene derivative of formula (4).

The halogenating agent used in this reaction includes iodine, bromine and chlorine. Particularly, bromine is preferably used. The amount thereof to be used is usually about 1 to 2 moles, preferably about 1.05 to 1.3 moles per mol of the triene derivative of formula (4).

In the reaction described above, an inert organic solvent is usually used, and examples of such an inert organic solvent include hydrocarbon solvents such as n-hexane, cyclohexane, n-pentane, n-heptane, benzene or the like.

ether solvents such as diethyl ether, tetrahydrofuran, dimethoxyethane, anisole or the like, halogenated solvents such as chloroform, dichloromethane, 1,2-dichloroethane, monochlorobenzene, o-dichlorobenzene or the like, and aprotic polar solvent such as acetonitrile, N,N-dimethylformamide, N,N-dimethylacetamide, hexamethylphosphoric triamide or the like. These can be used as an inert mixed solvent containing 2 or more of the solvents. For example, a solvent such as toluene having a hydrogen atom at the benzyl position may, depending on the reaction conditions, react with the halogenating agent to form benzyl halide, and thus such solvent is preferably used as an inert mixed solvent, for example, by mixing with acetonitrile and the like. Such an inert mixed solvent is not limited to the combination exemplified above.

The reaction temperature is usually in the range of −78° C. to the boiling point of the solvent used, preferably in the range of about −40 to 30° C.

After completion of the reaction, the resulting reaction mixture may be washed, if necessary, with an aqueous solution of sodium sulfite or sodium thiosulfate and extracted with an organic solvent, and the organic layer is concentrated to give the dihalogen derivative of formula (2). Further, this product can be purified by various kinds of chromatography, but the product is used preferably as it is in a crude form in the subsequent reaction.

The sulfone derivative of formula (1) in the present invention can be obtained by reacting the sulfone of formula (3) with the dihalogen derivative of formula (2) in the presence of a base.

The base to be used in this reaction includes an alkali metal alkoxide, an alkali metal hydride, alkyl lithium and a Grignard reagent. Specific examples thereof include sodium methoxide, potassium methoxide, sodium ethoxide, potassium ethoxide, potassium t-butoxide, sodium t-butoxide, sodium hydride, potassium hydride, n-butyl lithium, methyl magnesium bromide, methyl magnesium chloride, ethyl magnesium bromide, ethyl magnesium chloride and the like. The amount of the base to be used is about 1 to 5 moles per mol of the sulfone (3).

In the reaction described above, an organic solvent is usually used, and examples of such an organic solvent include aprotic polar solvents such as N,N-dimethylformamide, dimethyl sulfoxide, N,N-dimethylacetamide, acetonitrile, hexamethylphosphoric triamide or the like, hydrocarbon solvents such as n-hexane, n-heptane, cyclohexane, n-pentane, toluene, xylene or the like, and ether solvents such as diethyl ether, tetrahydrofuran, 1,4-dioxane, anisole or the like. A mixture of two or more of the solvents may also be used.

The reaction temperature is usually in the range of −78° C. to the boiling point of the solvent used, and lower temperatures, particularly −40° C. or less are preferred.

After the reaction, the sulfone derivative (1) can be obtained by carrying out conventional post-treatment such as extraction and various kinds of chromatography.

The protective group for the resulting sulfone derivative (1) can be removed suitably by acid or alkali hydrolysis or by ester exchange reaction by an acid or basic catalyst, if necessary. In addition, the benzyl group etc. can also be removed by hydrogenation or reduction reaction with alkali metal-ammonia. The silyl group can be removed, for example, by use of a solution of tetra-n-butyl ammonium fluoride in tetrahydrofuran or a mixed solution of acetic acid, water and tetrahydrofuran. With respect to the protective groups and deprotection reactions thereof, reference can be made to the disclosure of Greene: T. W. Protective Groups in Organic Synthesis, 3rd Edition (Wiley) and the like. The sulfone derivative of formula (1) wherein $R^1$ is a hydrogen atom can be obtained by performing the above-described de-protection reaction, if necessary.

Vitamin A can be obtained by allowing a base to react with the sulfone derivative (1) thus obtained.

Examples of the base to be used in this reaction include an alkali metal hydroxide, an alkali metal hydride and an alkali metal alkoxide, among which the alkali metal hydroxide and the alkali metal alkoxide are preferably used. Specific examples thereof include sodium hydroxide, potassium hydroxide, sodium methoxide, sodium ethoxide, potassium methoxide, potassium ethoxide, sodium t-butoxide, and potassium t-butoxide. The amount of the base to be used is usually about 2 to 20 moles per mol of the sulfone derivative (1).

In the reaction described above, an organic solvent is usually used, and such solvent includes hydrocarbon solvents such as n-hexane, n-heptane, cyclohexane, n-pentane, toluene, xylene or the like, ether solvents such as diethyl ether, tetrahydrofuran, dimethoxyethane, anisole or the like, and aprotic polar solvents such as acetonitrile, N,N-dimethylformamide, dimethyl sulfoxide, N,N-dimethylacetamide, hexamethylphosphoric triamide or the like. Preferred is cyclohexane.

The reaction temperature is usually in the range of −20° C. to the boiling point of the solvent used, preferably in the range of about 0 to 100° C. The reaction time is varied depending on the type of base and the reaction temperature used in the reaction, but is usually in the range about 1 to 24 hours.

After completion of the reaction, vitamin A can be obtained by carrying out conventional post-treatment. If necessary, the product can be purified by crystallization and various kinds of chromatography.

The resulting vitamin A can be introduced with a protective group for a hydroxyl group by a conventional manner, and for example, vitamin A acetate can be obtained by acetylation.

EXAMPLES

Hereinafter, the present invention is described in more detail by reference to the Examples, which however are not intended to limit the present invention. The structures of compounds (I) to (IV) described in the Examples are shown after the Examples.

Example 1

0.3 g (1.54 mmol) of triene (IV) was dissolved in 4 ml tetrahydrofuran and cooled to −60° C. under stirring, and a solution of 0.3 g (1.85 mmol) bromine in 2 ml acetonitrile was added dropwise thereto. Thereafter, the mixture was stirred at the same temperature for 5 hours. Then, the reaction mixture was poured into water and extracted with ethyl acetate. The organic layer was washed with an aqueous solution of sodium sulfite and then with an aqueous saturated solution of sodium chloride and dried over anhydrous magnesium sulfate, and the solvent was distilled off to give the dihalogen derivative (II) in about 94% yield.

$^1$H-NMR δ (CDCl$_3$) 1.73 (3H, s), 1.83 (3H, s), 2.05 (3H, s), 2.58 (1H, dd, J=8 Hz, 12 Hz), 2.73 (1H, dd, J=8 Hz, 12 Hz), 3.90 (1H, d, J=10 Hz), 3.95 (1H, d, J=10 Hz), 4.57 (2H, d, J=7 Hz), 4.80–4.86 (1H, m), 5.39–5.44 (1H, m), 5.75 (1H, d, J=7 Hz)

$^{13}$C-NMR δ (CDCl$_3$) 15.5, 16.9, 21.3, 39.6, 47.3, 49.3, 61.2, 123.0, 131.5, 135.8, 137.8, 171.3

Example 2

0.3 g (1.54 mmol) of triene (IV) was dissolved in 4 ml toluene and cooled to −20° C. under stirring. A solution of 0.3 g (1.85 mmol) bromine in 4 ml acetonitrile was added dropwise thereto at −20° C. Thereafter, the mixture was stirred at the same temperature for 5 hours. Then, the reaction mixture was poured into water and extracted with ethyl acetate. The organic layer was washed with an aqueous solution of sodium sulfite and then with an aqueous saturated solution of sodium chloride and dried over anhydrous magnesium sulfate, and the solvent was distilled off to give the dihalogen derivative (II) in about 90% yield.

Example 3

0.13 g (0.43 mmol) of sulfone (I) was dissolved in 3 ml N,N-dimethylformamide (DMF), and 3 ml solution of 0.36 g (0.87 mmol) of the dihalogen derivative (II) in DMF and 3 ml solution of 0.10 g (0.87 mmol) of potassium t-butoxide in DMF were simultaneously poured into it at −60° C., and thereafter, the mixture was stirred at the same temperature for 3 hours. Then, the reaction solution was poured into water and extracted with ethyl acetate. The organic layer was washed with an aqueous saturated solution of ammonium chloride and then with a saturated saline solution and dried over anhydrous magnesium sulfate, and the solvent was distilled off to give a crude product containing the sulfone derivative (III). The resulting crude product was subjected to a quantitative analysis by liquid chromatography, which showed that the reaction yield was 34%. The resulting crude product was purified by silica gel column chromatography to give the sulfone derivative (III).

$^1$H-NMR δ (CDCl$_3$) 0.87 (3H, s), 1.08 (3H, s), 1.41–1.64 (4H, m), 1.39 (3H, s), 1.84 (3H, s), 2.04 (3H, s), 2.06 (3H, s), 2.05–2.13 (2H, m), 2.42 (3H, s), 2.65 (1H, dd, J=7 Hz, 11 Hz), 3.09 (1H, dd, J=7 Hz, 11 Hz), 3.94 (1H, t, J=7 Hz), 4.72 (2H, d, J=7 Hz), 5.60 (1H, d, J=6 Hz), 5.88 (1H, d, J=10 Hz), 6.08–6.24 (2H, m), 7.27 (2H, d, J=8 Hz), 7.73 (2H, d, J=8 Hz)

$^{13}$C-NMR δ (CDCl$_3$) 11.2, 14.8, 17.6, 19.6, 20.1, 21.9, 26.8, 27.7, 33.1, 34.7, 38.3, 40.2, 59.8, 64.1, 123.2, 123.6, 127.2, 127.9, 128.0, 129.4, 132.8, 134.1, 136.2, 137.3, 137.9, 142.4, 169.5

HR-MS found 483.2569 (M−H)$^+$ calcd for C$_{29}$H$_{39}$O$_4$S 483.2559

Example 4

0.13 g (0.43 mmol) of sulfone (I) was dissolved in 3 ml DMF and cooled at −60° C. 3 ml solution of 0.10 g (0.87 mmol) potassium t-butoxide in DMF was added dropwise thereto at the same temperature, and then 3 ml solution of 0.36 g (0.87 mmol) of the dihalogen derivative (II) in DMF was added dropwise thereto. Thereafter, the mixture was stirred at the same temperature for 3 hours. The reaction solution was poured into water and extracted with ethyl acetate. The organic layer was washed with an aqueous saturated solution of ammonium chloride and then with a saturated saline solution and dried over anhydrous magnesium sulfate, and the solvent was distilled off to give a crude product containing the sulfone derivative (III). The resulting crude product was subjected to quantitative analysis by liquid chromatography, which showed that the reaction yield was 26%.

Example 5

The same reaction and post-treatment were conducted in the same manner as in Example 4 except that sodium t-butoxide was used in place of potassium t-butoxide, whereby a crude product containing the sulfone derivative (III) was obtained. The resulting crude product was subjected to quantitative analysis by liquid chromatography, which showed that the reaction yield was 25%.

Example 6

The same reaction and post-treatment were conducted in the same manner as in Example 4 except that 1.6 M n-butyl lithium solution in hexane was used in place of potassium t-butoxide, whereby a crude product containing the sulfone derivative (III) was obtained. The resulting crude product was subjected to quantitative analysis by liquid chromatography, which showed that the reaction yield was 15%.

Example 7

After 0.10 g (0.2 mmol) of the sulfone derivative (III) was dissolved in 3 ml cyclohexane, 0.14 g (2.1 mmol) potassium methoxide was added thereto and stirred at 40° C. for 5 hours. The reaction solution was poured into an aqueous saturated solution of ammonium chloride and extracted with ethyl acetate. The organic layer was washed with an aqueous saturated solution of ammonium chloride and dried over anhydrous magnesium sulfate followed by distilling off the solvent to give a crude red oily product. The resulting crude product was subjected to a quantitative analysis by liquid chromatography, which showed that the yield of vitamin A was 85%.

The structural formulae of the compounds in the Examples are as follows:

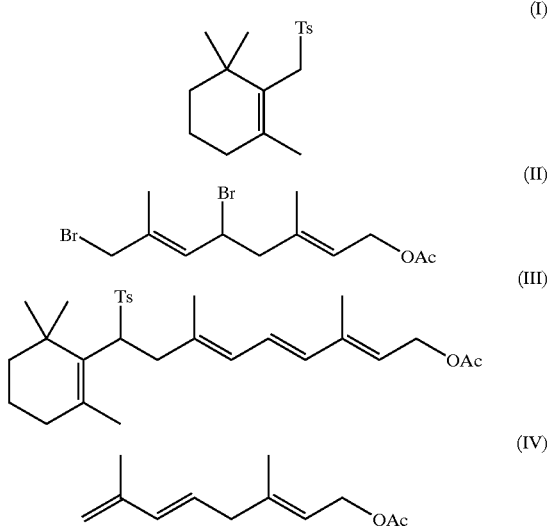

wherein Ts is a p-tolylsulfonyl group.

Industrial Applicability

According to the present invention, novel dihalogen derivatives and sulfone derivatives which are useful in the fields of pharmaceutical preparations, feed or food additives can be produced industrially advantageously from inexpensive starting materials.

What is claimed is:

1. A dihalogen derivative represented by formula (2):

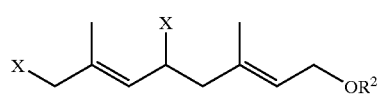

(2)

wherein X represents a halogen atom and $R^2$ represents a protective group for a hydroxyl group.

2. The dihalogen derivative according to claim 1, wherein X is a bromine atom.

3. A process for producing a dihalogen derivative represented by formula (2) as defined in claim 1, which comprises allowing a halogenating agent to react with a triene derivative represented by formula (4):

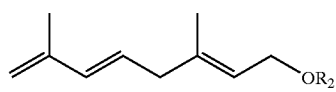

(4)

wherein $R^2$ represents a protective group for a hydroxyl group.

4. A process for producing a sulfone derivative represented by formula (1):

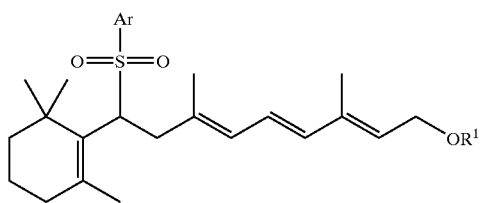

(1)

wherein Ar represents an aryl group which may have a substituent group, and $R^1$ represents a hydrogen atom or a protective group for a hydroxyl group, which comprises allowing a sulfone represented by formula (3):

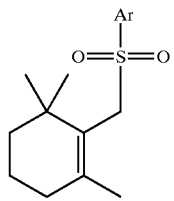

(3)

wherein Ar represents an aryl group which may have a substituent group, to react in the presence of a base with a dihalogen derivative represented by formula (2) as defined in claim 1.

5. The process according to claim 4, which further comprises the step of allowing the formed sulfone derivative of formula (1) to react with a base to give vitamin A.

6. The process according to claim 3, which further comprises the step of allowing the formed dihalogen derivative to react in the presence of base with a sulfone represented by formula (3):

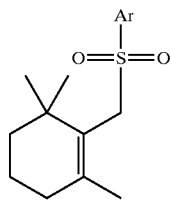

(3)

wherein Ar represents an aryl group which may have a substituent group, to give a sulfone derivative represented by formula (1):

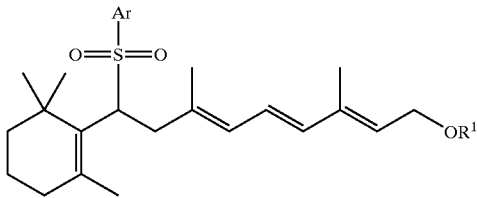

(1)

wherein Ar has the same meaning as defined above, and $R^1$ represents a hydrogen atom or a protective group for a hydroxyl group.

7. The process according to claim 6, which further comprises the step of allowing a sulfone derivative represented by formula (1) to react with a base to give vitamin A.

8. The process according to claim 4, 5, 6, or 7, wherein the reaction of a sulfone represented by formula (3) with a dihalogen derivative represented by formula (2) is conducted in the presence of a base selected from the group consisting of an alkali metal alkoxide, an alkali metal hydride, alkyl lithium and a Grignard reagent.

9. The process according to claim 4, 5, or 6, wherein X in the dihalogen derivative of formula (2) is a bromine atom.

10. The process according to claim 3 or 6, wherein the halogenating agent is bromine, and X in the dihalogen derivative of formula (2) is a bromine atom.

11. The process according to claim 3, 4, 5, or 6, wherein $R^2$ is an acetyl group.

12. The process according to claim 5, or 7, wherein a base selected from the group consisting of an alkali metal hydroxide, an alkali metal hydride and an alkali metal alkoxide is reacted with a sulfone derivative represented by formula (1).

* * * * *